US009017430B2

(12) United States Patent
Colucci et al.

(10) Patent No.: US 9,017,430 B2
(45) Date of Patent: *Apr. 28, 2015

(54) ALKANOLAMIDES AND THEIR USE AS FUEL ADDITIVES

(71) Applicant: Afton Chemical Corporation, Richmond, VA (US)

(72) Inventors: William J. Colucci, Glen Allen, VA (US); Abbas Kadkhodayan, Collinsville, IL (US)

(73) Assignee: Afton Chemical Corporation, Richmond, VA (US)

( * ) Notice: Subject to any disclaimer, the term of this patent is extended or adjusted under 35 U.S.C. 154(b) by 38 days.

This patent is subject to a terminal disclaimer.

(21) Appl. No.: 13/867,374

(22) Filed: Apr. 22, 2013

(65) Prior Publication Data

US 2013/0232860 A1 Sep. 12, 2013

Related U.S. Application Data

(63) Continuation of application No. 11/534,048, filed on Sep. 21, 2006, now Pat. No. 8,444,720.

(51) Int. Cl.
*C10L 1/22* (2006.01)
*C10L 1/24* (2006.01)
*C10L 1/224* (2006.01)
*C07C 231/02* (2006.01)
*C10L 10/00* (2006.01)
*C10L 10/08* (2006.01)
*C10L 10/18* (2006.01)

(52) U.S. Cl.
CPC ............. *C10L 1/224* (2013.01); *C07C 231/02* (2013.01); *C10L 1/221* (2013.01); *C10L 10/00* (2013.01); *C10L 10/08* (2013.01); *C10L 10/18* (2013.01)

(58) Field of Classification Search
USPC .................................. 44/418, 419
See application file for complete search history.

(56) References Cited

U.S. PATENT DOCUMENTS

| 2,607,740 | A |   | 8/1952  | Vitale et al.         |
|-----------|---|---|---------|-----------------------|
| 2,844,609 | A |   | 7/1958  | Tesoro                |
| 4,330,339 | A | * | 5/1982  | Nimerick ........ 106/243 |
| 4,729,769 | A |   | 3/1988  | Schlicht et al.       |
| 4,885,008 | A |   | 12/1989 | Ishizaki et al.       |
| 6,511,520 | B1| * | 1/2003  | Eber et al. ....... 44/388 |
| 6,562,082 | B1|   | 5/2003  | Leaver et al.         |
| 6,562,086 | B1| * | 5/2003  | Gentry et al. ..... 44/418 |
| 6,589,302 | B1|   | 7/2003  | DeRosa et al.         |
| 6,866,690 | B2|   | 3/2005  | Aradi et al.          |
| 2008/0072477 | A1 |  | 3/2008 | Colucci et al.       |

FOREIGN PATENT DOCUMENTS

| EP | 0905125      |   | 3/1999  |
|----|--------------|---|---------|
| EP | 0957152      |   | 11/1999 |
| EP | 1688414 A2   |   | 8/2006  |
| FR | 2772784 A1   | * | 6/1999  |
| GB | 693086 A     |   | 6/1953  |
| GB | 751801 A     |   | 7/1956  |
| GB | 781549 A     |   | 8/1957  |
| GB | 2252555 A    |   | 8/1992  |
| WO | 9900467 A1   |   | 1/1999  |
| WO | 0220703      |   | 3/2002  |
| WO | 2008057455 A2|   | 5/2008  |

OTHER PUBLICATIONS

European Search Report, dated Sep. 2, 2010, European Patent Application No. 07252256.8, filed Jun. 5, 2007, pp. 1-15, published by the European Patent Office.

* cited by examiner

*Primary Examiner* — James Goloboy
*Assistant Examiner* — Latosha Hines
(74) *Attorney, Agent, or Firm* — Fitch, Even, Tabin & Flannery LLP, Dennis Reinear

(57) ABSTRACT

The present invention relates to alkanolamide-containing compositions, and more particularly to alkanolamide-containing compositions formed by the reaction of a fatty acid and diethanolamine (DEA) which contain low levels of undesirable by-products. Such compositions are particularly suitable for use as fuel additives.

38 Claims, No Drawings

This application is a continuation of U.S. patent application Ser. No. 11/534,048, filed on Sep. 21, 2006, which is incorporated herein by reference in its entirety.

ALKANOLAMIDES AND THEIR USE AS FUEL ADDITIVES

CROSS-REFERENCE TO RELATED APPLICATIONS

This application is a continuation of U.S. patent application Ser. No. 11/534,048, filed on Sep. 21, 2006, which is incorporated herein by reference in its entirety.

FIELD OF INVENTION

The present invention relates to alkanolamide-containing compositions, and more particularly to alkanolamide-containing compositions formed by the reaction of a fatty acid and diethanolamine (DEA) which contain low levels of undesirable by-products. Such compositions are particularly suitable for use as fuel additives. The invention also relates to methods for reducing friction in diesel fuels, improving fuel economy in gasoline fuels, and providing anti-aging or stability control to fuels in general.

BACKGROUND OF THE INVENTION

Liquid hydrocarbon fuel burning engines are used in a wide variety of applications including automotive, transportation, marine, electricity generation and compressors. Such engines are often relatively inefficient and may emit significant quantities of pollutant gases and particles. This is of particular concern when the engines are used in built up areas, e.g. cities where the resultant pollution affects significant numbers of people, but is also of significant concern in other situations.

Liquid hydrocarbon fuels typically include a number of additives to improve the efficiency of combustion, reduce pollutant levels, modify combustion characteristics of the fuel and maintain engine cleanliness.

Dispersants and detergents, for example low molecular weight amines, are used to improve engine cleanliness. Additives which can reduce friction levels or otherwise improve efficiency in an engine are of particular interest as they can improve fuel economy. Even small improvements in efficiency would have massive impacts on a global scale.

One family of chemicals which it has been discovered has significant utility as fuel additives are alkanolamides formed by the reaction of fatty acids with diethanolamine (DEA). These additives are particularly suitable for use as additives to gasoline fuels but also may be suitable for use in other liquid hydrocarbon fuels, such as diesel. However, there is a significant problem with existing methods of manufacture of alkanolamides and the by-products formed thereby. It has been found that by-products are prone to form throughout the reaction process. A particularly significant impurity, bis-hydroxyethyl piperazine (BHEP), is formed via dimerisation of two DEA molecules. BHEP crystallizes out of the composition, particularly if present in concentrations of over 5000 ppm, though lower concentrations may also be problematic in some circumstances. This has significant implications in that, when the composition is used as a fuel additive, BHEP may block fuel inlets or cause other undesirable build ups in the engine. Additionally, crystallization of BHEP out of the composition may result in an end user perceiving problems with the composition as deposits of BHEP appearing in, for example, barrels of the composition would give the appearance of a contaminated or faulty batch, even if there would be no deleterious effects of the BHEP in use. Thus the effects of significant BHEP presence in an alkanolamide composition make it an undesirable constituent.

Accordingly, it is desirable to provide a composition comprising an improved alkanolamide, which contains a reduced amount of undesirable reaction by-products, particularly BHEP, and which will be suitable for use as a liquid hydrocarbon fuel additive.

SUMMARY OF THE DISCLOSURE

According to the present disclosure there is provided a composition comprising an alkanolamide, produced by the method comprising the steps of:
  a) combining DEA and a fatty acid at a low addition rate to form a mixture of fatty acid and DEA wherein the total molar quantity of fatty acid in the mixture is in excess of the total molar quantity of DEA in the mixture;
  b) applying at least a partial vacuum to the mixture; and
  c) maintaining the mixture at a suitable temperature and reduced pressure and for sufficient time for the reaction to proceed to form the composition.

By "DEA" and/or "diethanolamine" herein is meant any molecule or source of $H\text{---}N\text{---}(CH_2CH_2OH)_2$ and any or all precursors thereof able to generate same in situ, or mixtures comprising same. This can include, for example and not as a limitation herein, the diethanol amine salt of a Lewis acid.

The reaction should generally proceed to form the alkanolamide at a desired quality. Typically this is achieved when the DEA quantity has decreased to an acceptable level, e.g. 2% or less, preferably 1% or less.

A low rate of addition of DEA, the non-stoichiometric conditions (i.e. excess fatty acid) and/or application of a pressure reduction have been practiced in the past to reduce the rate of production and/or total amount of BHEP. Use of such reaction parameters means that levels of undesirable BHEP significantly below 5000 ppm can be achieved. Optimization of the method means that BHEP levels of 3000 ppm or below are easily achievable. In general it is desirable to reduce BHEP levels as far as possible, but the disadvantages of a slight BHEP level must be balanced with the efficiency of the process overall. BHEP levels of 3000 ppm or below are in many cases satisfactory as the tendency of BHEP to crystallize out of the composition is significantly reduced or removed at such levels. However, compositions containing BHEP at levels of 2000 ppm or below are desirable in certain circumstances.

Suitably the total amount of fatty acid with respect to DEA is in one embodiment in the range of molar ratios of about 1:0.4-1.0 (fatty acid:DEA), and in another embodiment in the range of about 1:0.5-0.85, yet another embodiment about 1:0.6-0.8, such as about 1:0.7.

Suitable addition rates for DEA lie from about 0.0001% of total DEA per minute to about 10% total DEA per minute, preferably from about 0.001% to about 5%, more preferably from about 0.001% to about 1%, particularly from about 0.002% to about 0.5%. In general a slower addition rate is preferred in order to minimize BHEP accumulation, but this must be balanced against drawing the time taken to produce a batch of the composition out to an unacceptable or uneconomic duration.

In one embodiment of the present disclosure both the addition of DEA to the fatty acid and the reaction (i.e. the time at reaction temperature) are conducted under a vacuum. However, in some embodiments it may be satisfactory if the addition of DEA is not conducted under a vacuum, or may be at a lesser vacuum than the reaction. Suitably the vacuum is an absolute pressure of 500 mm Hg (absolute pressure) or lower, preferably 250 mm Hg or lower, more preferably 125 mm Hg or lower especially 50mm Hg or lower. In general a greater (deeper) vacuum is useful in terms of accelerating the reaction process and limiting BHEP production. However, it may be desirable to reduce the vacuum (i.e. increase the pressure) during the addition of the DEA or at other points during the reaction to reduce foaming. Suitably the vacuum is maintained for a substantial portion of the reaction, preferably for essentially the entire time of the reaction. The pressure reduction can be maintained for substantially the entire time of the reaction and substantially the entire time of addition of the DEA to the fatty acid.

Suitably the reaction is conducted at a temperature of from about 100° C. to about 170° C., preferably from about 125° C. to about 160° C., more preferably from about 145° C. to about 155° C., particularly from about 148° C. to about 152° C. In one embodiment this temperature is maintained for substantially the entire time of the reaction.

It is preferred that the reaction proceeds for not longer than 16 hours, preferably 12 hours or less, more preferably 8 hours or less, especially 6 hours or less. If the reaction proceeds for longer than 16 hours an excessive build up of BHEP is generally observed. The time of the reaction proceeding is generally taken to be the time for which the temperature is maintained at the desired reaction temperature (i.e. in a preferred embodiment, at between 148° C. to 152° C.). In general the DEA is added to the fatty acid at a temperature below the reaction temperature, typically around 135° C. to 140° C. The heat produced by the exothermic reaction between DEA and fatty acid can then be used to raise the temperature to the reaction temperature; it is of course possible to cool the mixture or provide additional heat to maintain the reaction at the desired temperature. Thus the time of the reaction may in many cases be taken to run from the end of the addition of DEA until the time when the reaction is stopped, i.e., allowed to cool.

The term fatty acid as used herein refers to aliphatic mono-, di-, and poly carboxylic acids and derivatives thereof, e.g. fatty acid methyl, ethyl and/or isopropyl esters, or fatty acid mono-, di- and triglycerides. The term fatty acid can include a mixture of two or more fatty acids and derivatives thereof.

Preferred fatty acids for use in the present disclosure suitably can contain from 8 to 24, preferably from 10 to 22, more preferably from 12 to 20, and particularly from 12 to 18 carbon atoms.

Suitable fatty acids can be obtained from natural sources such as, for instance, plant or animal esters (e.g. palm oil, rape seed oil, palm kernel oil, coconut oil, babassu oil, soyben oil, castor oil, tallow, whale or fish oils, grease, lard, and mixtures thereof). The fatty acids can also be synthetically prepared, for example as described in "Fatty Acids in Industry", Ed. Robert W Johnson, Earl Fritz, Marcel Dekker Inc, 1989 ISBN 0-8247-7672-0.

Accordingly, suitably fatty acids include cocoate, capric, lauric, myristic, palmitic, stearic, oleic, linoleic, arachidonic, erucic and/or behenic acids or a mixture of two or more thereof. Specific branched chain fatty acids suitable for use in the present invention include iso-acids such as isostearic acid, isopalmitic acid, isomyristic acid, isoarachidic and isobehenic acid; neo acids such as neodecanoic acid; and other acids such as 2-ethyl hexanoic acids. Particularly suitable branched chain fatty acids contain alkyl side branches (attached directly to a carbon atom of the longest linear chain) having on average less than 5, preferably less than 3, more particularly in the range of 1.05 to 2, especially 1.1 to 1.5 carbon atoms, i.e. the side branches are predominantly methyl groups.

A particularly effective fatty acid for use in the method and compositions of the present disclosure is isostearic acid (ISAC), such as commercially available materials Prisorine™ 3501, 3502, 3503 or 3505 (ex Uniqema).

To achieve particularly low levels of BHEP it is preferred that the reaction is conducted at as low a pressure as possible, the DEA is added as slowly as possible, the temperature is maintained at between 148° C. to 152° C. for the duration of the reaction and that the reaction is not allowed to proceed beyond 16 hours. Each of these conditions is believed to have a role in accelerating progress of the reaction and/or limiting accumulation of BHEP. Accordingly, the best results would be obtained where all the above conditions are applied and optimized, but satisfactory results may be obtained without all of the above conditions being applied, or where one or more of them is not optimized.

In preparing the compositions of the present disclosure, the following steps are useful:
(a) sampling the mixture as the reaction progresses;
(b) determining the acid number of the sample; and
(c) halting the reaction once the acid number drops to 1.2, or halting the reaction once the acid number is below 2 and the acid number does not vary by greater than 0.1 from a previous sample.

The reaction product produced herein as a composition is in one embodiment a liquid hydrocarbon and in another embodiment is or comprises a solid or semi-solid hydrocarbon that is soluble or dispersible in the desired fuel. This composition reaction product comprises alkanolamide diol, alkanolamide diester, alkanolamide monoester, and mixtures thereof.

Suitably the previous sample is taken from 20 minutes to 2 hours previously, preferably from 40 minutes to 1 hour and 20 minutes previously, and conveniently about 1 hour previously.

According to a further aspect, the present disclosure also provides a composition comprising an alkanolamide which is the product of a reaction between a fatty acid and DEA, wherein the composition contains less than 5000 ppm of BHEP.

In another embodiment the composition comprises less than 3000 ppm of BHEP, and in yet a third embodiment less than 2000 ppm. These compositions are useful as fuel additives for achieving improved fuel economy in gasoline engine, improved fuel lubricity in low-sulfur (and ULSD) diesel fuels, and as an anti-aging agent for shelf life and stability control of a fuel.

Thus by the present disclosure are provided methods for achieving improved fuel economy in gasoline engine, methods for achieving improved fuel lubricity in low-sulfur (and ULSD) diesel fuels, and methods for achieving anti-aging or improved shelf life and/or stability control of a fuel by the incorporation into the fuel of the alkanolamide compositions produced according to the present disclosure.

Thus, there is also provided by the present disclosure a finished fuel product containing, inter alia, a major amount of a fuel, such as a gasoline or a diesel fuel, and a minor amount of an alkanolamide composition, wherein the alkanolamide composition has less than 5000 ppm pf BHEP. In other embodiments the amount of BHEP in the alkanolamide in the finished fuel product is less than 3000 and less than 2000 ppm.

The base fuels used in formulating the fuel compositions according to the present disclosure include any base fuels suitable for use in the operation of spark-ignition internal combustion engines, such as leaded or unleaded motor and aviation gasolines, diesel, and so-called reformulated gasolines which typically contain both hydrocarbons of the gasoline boiling range and fuel-soluble oxygenated blending agents, such as alcohols, ethers and other suitable oxygen-containing organic compounds. Suitable oxygenates include, for example, methanol, ethanol, isopropanol, t-butanol, mixed $C_1$ to $C_5$ alcohols, methyl tertiary butyl ether, tertiary amyl methyl ether, ethyl tertiary butyl ether, and mixed ethers. Oxygenates, when used, will normally be present in the base fuel in an amount below about 25% by volume, for example in an amount that provides an oxygen content in the overall fuel in the range of about 0.5 to about 5% by volume.

Fuel compositions may comprise a major amount of a base fuel and a minor amount of a fuel additive composition. A "major amount" may be understood to mean greater than or equal to about 50%. A "minor amount" may be understood to mean less than about 50%.

In one embodiment the composition is the product of the method set out above in more detail. The alkanolamide composition of the present disclosure in one embodiment has the following physical properties:

Appearance: Clear amber, viscous liquid
Acid number (mg KOH/g): 2.0 max
Alkali value (kg KOH/g): 30 max
DEA Content (%): 1.0 max
Flash point, °F. (PMCC): 220 min
BHEP content: <5000 ppm
Water content: 0.1 max Of these properties the most significant are BHEP content and DEA content, and the other physical properties are indicators of particular suitability. Accordingly, in one embodiment of the present invention the composition has BHEP content of <5000 ppm and a DEA content of ≤1%.

According to a further aspect of the present invention there is provided a fuel additive which is or includes a composition comprising an alkanolamide which is the product of a reaction between a fatty acid and DEA, wherein the composition contains less than 5000 ppm of BHEP, preferably less than 3000 ppm of BHEP, especially less than 2000 ppm. In one embodiment the alkanolamide is prepared by the method(s) disclosed herein.

Further details of a suitable composition are given above.

According to a further aspect the present disclosure provides a liquid hydrocarbon fuel which includes a compound comprising an alkanolamide which is the product of a reaction between a fatty acid and DEA, wherein the composition contains less than 5000 ppm of BHEP, preferably less than 3000 ppm of BHEP, especially less than 2000 ppm. In another embodiment the liquid hydrocarbon fuel is a gasoline grade of fuel. In an alternative embodiment the fuel is a diesel grade of fuel. Suitable gasoline or diesel fuels include those suitable for use in, for example, generators, stationary burners and home heating units, commercial transportation or domestic automotive engines (such as trucks and cars), marine engines, and/or compressors.

Suitably the composition can if desired comprise from about 0.1% to about 5% of the fuel by volume, or from about 0.5% to about 4%, or from about 0.75% to about 3%, especially from about 1% to about 2%.

According to a further aspect the present invention provides the use of a composition comprising an alkanolamide which is the product of the reaction between a fatty acid and DEA, wherein the reaction product contains less than 5000 ppm of BHEP, preferably less than 3000 ppm of BHEP, especially less than 2000 ppm, as a hydrocarbon fuel additive. In one embodiment the compound may be used as a friction modifying agent. In another embodiment the compound may be used to improve fuel economy of the combusting unit. Yet another utility of the alkanolamide produced according to the present disclosure is as an anti-valve sticking agent.

In a further embodiment herein is provided a method to reduce or eliminate valve sticking in an engine combusting a fuel and having intake valves and/or exhaust valves, comprising fueling and operating said engine with a fuel composition comprising an alkanolamide which is the product of the reaction between a fatty acid and DEA, wherein the reaction product contains less than 5000 ppm of BHEP, preferably less than 3000 ppm of BHEP, especially less than 2000 ppm.

Embodiments of the present invention will now be described by way of example only. It should be noted that the described embodiments do not limit the scope of the invention.

DESCRIPTION OF THE PREFERRED EMBODIMENTS

Example of Composition Production Process

An example of a process for manufacturing a composition in accordance with the present invention involves a reaction producing a DEA amide (i.e. an alkanolamide). The reaction of fatty acid and diethanolamine (DEA) forms DEA amides and water. The by-product water can be removed by vacuum stripping, i.e. distillation.

During the reaction to form the alkanolamide from a fatty acid and DEA, it has been observed that an impurity that is a derivative of piperazine, bis-hydroxyethyl piperazine (BHEP), forms over the course of the reaction. BHEP can precipitate out of the reaction product over time, particularly at concentration over 5000 ppm so it is essential to keep this by-product under control. The formation of this undesirable by-product presents a significant problem in the manufacture of alkanolamides. To limit the level of this impurity, according to the present disclosure, a number of steps are taken during the manufacturing process.

The time at temperature (i.e. reaction time) for this reaction is generally limited to 16 hours and preferably significantly less. Running the reaction beyond 16 hours causes a build up of BHEP and should thus generally be avoided.

It should be noted that this reaction provides an exception to the general trend of alkali number drift in other related products. The alkali number of the product of this reaction generally remains stable because of reaction conditions that leave virtually no free DEA in the product.

An exemplary reaction process can be summarized as follows:

The diethanolamine DEA is kept molten by maintaining at 38±5.5° C. (100±10° F.).
The reactor is set up ready to receive the reactants (a suitable reactor may be a R3200 reactor).
The reactor is charged with the fatty acid, i.e. isostearic acid (e.g. isostearic available under trade name Prisorine™ 3501, 3502, 3503 or 3505 (ex Uniqema)). The isostearic acid can be added at the maximum rate for the particular reactor. Obviously the amount of reactants will be changed to suit the volume of the particular reactor, whilst maintaining the desired ratio of reactants.
The agitator is set to run at a suitable rate to achieve satisfactory mixing of the mixture.
The reactor is heated to 138° C. (280° F.). The reactor heater can then be switched off. The exothermic reaction of the fatty acid and DEA will elevate temperature to the desired level for the reaction.
The reactor is charged with DEA, to give a molar ratio of 1:0.7 (isostearic acid:DEA). The DEA should be added slowly, e.g. at a rate of around 25 lbs/min for a total DEA load of 7690 lbs (3488 kg)—which would correspond to a isostearic acid load of 32310 lbs (14656 kg).

The reaction will be heated to 149° C. (300° F.) at rate of 0.8° C./min (1.5° F./min) and the water distillation is started. The heating is generally provided by the exothermic reaction between the fatty acid and DEA, but additional heating or cooling can be provided if required to achieve and/or maintain the desired temperature. Excessive foam build up at the beginning of distillation should be watched for.

When the temperature reaches 149° C. (300° F.) the time is recorded. This is used to track the total time at temperature for the batch (i.e. "reaction time").

The reactor is held at 149° C. (300° F.) and the vacuum is brought down to the desired level (e.g. below 50 mm Hg). It is important to observe for excessive foam build up at the beginning of vacuum ramp.

Once full vacuum has been reached, the conditions are held. The temperature should not be allowed to exceed 153° C. (307.5° F.).

The mixture within the reactor is sampled regularly to check reaction progress (e.g. hourly).

When each sample is taken the total time for the batch at 149° C. (300° F.) is recorded. The results of the sample analysis are logged. Suitable acid and alkali number end parameters for the reaction product are:
Acid Number: 2.0 max
Alkali Number: 30 max Each sample is compared with the following parameters to determine if the reaction end point is reached. If one of the three batch parameters is met then the next step in the process should be proceeded to. If none of the three following parameters are met, the reaction conditions should be maintained and the batch re-sampled later. There are, in general no running adjustments to the batch. The reaction parameters used to mark the end point are as follows:
The acid number is 1.2 or less;
The acid number is 2.0 or less and within 0.1 units of the acid number of the previous sample; or
The total time for the batch at 149° C. (300° F.) reaches 16 hours.

Once one of the three criteria above is met, the mixture is cooled and the vacuum is broken.

The reaction mixture is again sampled to check the final batch properties and the results logged. The results should be within the following parameters:
Gardner Color: 5 max
Acid no.: 2.0 max
Alkali no.: 30 max
Water(%): 0.1 max Assuming the batch is within specification, the reaction product is then transferred from the reactor to barrels or other containers as appropriate.

Such a method as described above is capable of producing an alkanolamide-containing composition with a BHEP content of less than 3000 ppm as determined by gas chromatography. It may be possible that further optimization of the process may result in even lower levels of BHEP, and such an optimized process is within the scope of the present invention.

Comparative Example

As a control reaction the process described above was repeated with the following differences:
A stoichiometric mixture of DEA and isostearic acid was used (i.e. a 1:1 molar ratio).
The DEA was not added slowly, but rather at the maximum rate achievable with the reactor. Otherwise the reaction conditions were identical.

The product of this reaction typically contains at least 6000 ppm BHEP. When the product is stored in barrels for a period of two weeks, significant deposits of BHEP developed on the sides of the barrel.

Production of a Modified Fuel

The composition as produced in the above method is particularly suitable for use as a fuel additive for gasoline fuel. To form a modified fuel between 1 and 2% by volume of the composition can in one embodiment be added to gasoline fuel.

The modified fuel produced has several advantageous properties, including but not limited to, reducing friction within the engine in which it is used, thus increasing efficiency.

Three engine valve sticking experiments were performed. These had two levels of BHEP contamination in the diethanolamide fuel additive. One level was 1965 ppm of BHEP and the other two experiments had 3664 ppm of BHEP in the gasoline. The sample containing the 1965 ppm BHEP was found to provide the best passing rate on all relevant fuel and engine compression tests. Modifications to the described examples may be made without departing from the scope of the present invention.

The invention claimed is:

1. A method of making a fuel additive comprising an alkanolamide, the method comprising:
   (a) adding diethanolamine (DEA) to a fatty acid at a rate of from 0.0001% of total DEA per minute to about 5% total DEA per minute to form a mixture of fatty acid and DEA wherein the total molar quantity of fatty acid in the mixture is in excess of the total molar quantity of DEA;
   (b) applying a vacuum to the mixture; and
   (c) maintaining the mixture at a temperature suitable for reacting the DEA with the fatty acid to form an alkanolamide and a bis-hydroxyethyl piperazine (BHEP) by-product while adding the DEA wherein the fuel additive contains less than 3000 part per million (ppm) of bis-hydroxyethyl piperazine (BHEP).

2. The method of claim 1, wherein the fatty acid is selected from the group consisting of cocoate, capric, lauric, myristic, palmitic, stearic, oleic, linoleic, arachidonic, erucic and behenic acids and mixtures thereof.

3. The method of claim 1, wherein the fatty acid is isostearic acid.

4. The method of claim 1, wherein the DEA is added at a rate of from about 0.001% of total DEA per minute to about 1% of total DEA per minute.

5. The method of claim 1, wherein the DEA is added at a rate of from 0.002% of total DEA per minute to 0.5% total DEA per minute.

6. The method of claim 1, wherein the total amount of fatty acid with respect to DEA is in the range of molar ratios of about 1:0.4-1.0 (fatty acid:DEA).

7. The method of claim 1, wherein the range of molar ratios is about 1:0.5-0.85 (fatty acid:DEA).

8. The method of claim 1, wherein the range of molar ratios is about 1:0.6-0.8 (fatty acid:DEA).

9. The method of claim 1, wherein the range of molar ratios is about 1:0.7 (fatty acid:DEA).

10. The method of claim 1, wherein the composition is maintained at a pressure of about 500 mm Hg or less for a substantial portion of the time of the reaction.

11. The method of claim 1, wherein the composition is maintained at a pressure of about 250 mm Hg or less for a substantial portion of the time of the reaction.

12. The method of claim 1, wherein the composition is maintained at a pressure of about 125 mm Hg or less for a substantial portion of the time of the reaction.

13. The method of claim 1, wherein the composition is maintained at a pressure of about 50 mm Hg or less for a substantial portion of the time of the reaction.

14. The method of claim 1, wherein the pressure is maintained for essentially the entire time of the reaction.

15. The method of claim 1, wherein the pressure is maintained for essentially for the entire time of the reaction and the entire time of the addition of the DEA.

16. The method of claim 1, wherein the mixture is maintained at a temperature of from about 100° C. to about 170° C.

17. The method of claim 1, wherein the mixture is maintained at a temperature of from about 125° C. to about 160° C.

18. The method of claim 1, wherein the composition is maintained at a temperature of from about 145° C. to about 155° C.

19. The method of claim 1, wherein the composition is maintained at a temperature of from about 148° C. to about 152° C. for not more than 16 hours.

20. The method of claim 1, wherein the diethanolamine is a diethanol amine salt of a Lewis acid.

21. A fuel additive comprising an alkanolamide which is the product of a reaction between a fatty acid and DEA, wherein the fuel additive contains less than 3000 part per million (ppm) of bis-hydroxyethyl piperazine (BHEP).

22. A fuel mixture comprising:
a major amount of a hydrocarbon fuel; and
a fuel additive comprising an alkanolamide that is the product of a reaction between a fatty acid and DEA, wherein the fuel additive included less than 3000 part per million (ppm) of bis-hydroxyethyl piperazine (BHEP) prior to mixing of the additive with the hydrocarbon fuel.

23. The fuel mixture of claim 22, wherein the hydrocarbon fuel is gasoline.

24. The fuel mixture of claim 22, wherein the hydrocarbon fuel is diesel.

25. The fuel mixture of claim 22, further comprising a fuel soluble oxygen-containing organic compound.

26. The fuel mixture of claim 22, wherein the fuel additive is in a concentration of about 0.1% to about 5% by volume of the fuel mixture.

27. A fuel additive prepared by the method comprising:
(a) adding diethanolamine (DEA) to a fatty acid to form a mixture of fatty acid and DEA wherein the total molar quantity of fatty acid in the mixture is in excess of the total molar quantity of DEA;
(b) applying a vacuum to the mixture; and
(c) maintaining the mixture at a suitable temperature and for sufficient time for a reaction to proceed to form the composition,
wherein the fuel additive comprises an alkanolamide and less than 3000 part per million (ppm) of bis-hydroxyethyl piperazine (BHEP).

28. The fuel additive of claim 27, wherein the fatty acid is selected from the group consisting of cocoate, capric, lauric, myristic, palmitic, stearic, oleic, linoleic, arachidonic, erucic and behenic acids and mixtures thereof.

29. The fuel additive of claim 27, wherein the fatty acid comprises isostearic acid.

30. The fuel additive of claim 27, wherein the total amount of fatty acid with respect to DEA is in the range of molar ratios of about 1:0.4-1.0 (fatty acid:DEA).

31. The fuel additive of claim 27, wherein the fuel additive contains less than 2000 ppm of BHEP.

32. The fuel additive of claim 27, wherein the DEA content is less than 1.0%.

33. A composition prepared by the method comprising the steps of:
(a) adding diethanolamine (DEA) to a fatty acid to form a mixture of fatty acid and DEA wherein the total molar quantity of fatty acid in the mixture is in excess of the total molar quantity of DEA;
(b) applying a vacuum to the mixture; and
(c) maintaining the mixture at a suitable temperature and for sufficient time for a reaction to proceed to form the composition,
wherein the composition contains less than 3000 part per million (ppm) of bis-hydroxyethyl piperazine (BHEP).

34. The composition of claim 33, wherein the fatty acid is selected from the group consisting of cocoate, capric, lauric, myristic, palmitic, stearic, oleic, linoleic, arachidonic, erucic and behenic acids and mixtures thereof.

35. The composition of claim 33, wherein the fatty acid comprises isostearic acid.

36. The composition of claim 33, wherein the total amount of fatty acid with respect to DEA is in the range of molar ratios of about 1:0.4-1.0 (fatty acid:DEA).

37. The composition of claim 33, wherein the fuel additive contains less than 2000 ppm of BHEP.

38. The composition of claim 33, wherein the DEA content is less than 1.0%.

* * * * *